United States Patent [19]

Bryant

[11] Patent Number: 4,561,450
[45] Date of Patent: Dec. 31, 1985

[54] ELECTROLYTIC PRESSURE TRANSDUCTION SYSTEM

[75] Inventor: Gordon H. Bryant, Kailua, Hi.

[73] Assignee: The United States of America as represented by the Secretary of the Army, Washington, D.C.

[21] Appl. No.: 657,438

[22] Filed: Oct. 3, 1984

[51] Int. Cl.$^4$ ............................................. A61B 5/00
[52] U.S. Cl. ................................................... 128/780
[58] Field of Search .................... 128/748, 783–786, 128/642, 715, 670, 780; 73/753–754, 756

[56] References Cited

U.S. PATENT DOCUMENTS

| | | | |
|---|---|---|---|
| 3,437,088 | 4/1969 | Bielinski | 128/780 |
| 3,480,003 | 11/1969 | Crites | 128/780 |
| 3,939,823 | 2/1976 | Kaye et al. | 128/748 |
| 3,970,862 | 7/1976 | Edelman et al. | 128/748 X |
| 4,030,481 | 6/1977 | Hill | 128/748 |
| 4,073,287 | 2/1978 | Bradley et al. | 128/642 |
| 4,136,681 | 1/1979 | Hon | 128/748 |
| 4,168,703 | 9/1979 | Kenigsberg | 128/748 |
| 4,214,593 | 7/1980 | Imbruce | 128/740 |
| 4,456,013 | 6/1984 | De Rossi et al. | 128/675 |
| 4,461,304 | 7/1984 | Kuperstein | 128/642 |
| 4,476,872 | 10/1984 | Perlin | 128/642 |
| 4,484,585 | 11/1984 | Baier | 128/748 |

OTHER PUBLICATIONS

Borky et al., "Integrated Signal Conditioning for Silicon Pressure Sensors"; *IEEE Trans. on Electron Devices*, vol. ED-26, No. 12, 12-1979, pp. 1906-1910.

*Primary Examiner*—Lee S. Cohen
*Assistant Examiner*—Angela D. Sykes
*Attorney, Agent, or Firm*—John H. Raubitschek; Arthur I. Spechler; Francis A. Cooch

[57] ABSTRACT

This invention is directed to a Wheatstone bridge circuit for measuring pressure in the distal esophageal sphincter (D.E.S.) as well as in other organs and bodily cavities. A flexible hollow tube having three spaced electrodes is lodged in the esophagus. The tube is partly filled with a saline solution to cover the electrodes, thereby producing two series connected, pressure sensitive resistors. The electrolytic resistors are coupled to two series connected fixed resistors to complete the bridge circuit. Electrical imbalances in the bridge circuit are measured in terms of the pressure corresponding to the pressure applied by the D.E.S.

7 Claims, 4 Drawing Figures

ELECTROLYTIC PRESSURE TRANSDUCTION SYSTEM

BACKGROUND OF THE INVENTION

This invention relates to pressure measuring apparatus and, more specifically to a Wheatstone bridge with electrolytic resistances for measuring pressure within bodily cavities and passageways, and the like.

There are many reasons for measuring pressure within bodily cavities and passageways. Illustratively, the muscular action of the esophagus in conveying food from the mouth to the stomach, frequently referred to as gastric motility, is a matter of major medical interest. The action of the esophagus in transferring bites of food from the mouth to the stomach can be likened to a pump in which a "valve" in the throat (the crycopharyngeal sphincter) cooperates with the longitudinal and circumferential muscles associated with the esophagus and another "valve" at the opposite end of the esophagus (the distal esophageal sphincter, or D.E.S.). On swallowing, the crycopharyngeal sphincter opens to pass through a food portion and then closes. A wave of relaxation in the muscles associated with the esophagus moves the food downwardly toward the stomach and, passing the D.E.S., enters the stomach. The D.E.S., in turn, should be capable of retaining the stomach contents in the stomach in all reasonable circumstances.

Stomach contents do, however, flow back into the esophagus (i.e., reflux) in some circumstances and produce "heartburn". Generally, this failure to retain the stomach contents in the stomach may be a consequence of inadequate gastric motility and failure of the D.E.S.

To diagnose esophageal problems, several techniques are available to medical science, including motility studies that require pressure measurements in the alimentary tract. Several devices have been proposed to take these important measurements. A tube, for instance, that has a closed lower end is provided with a number of longitudinally spaced side holes. This tube is lodged in the alimentary tract with the longitudinally spaced holes each in alignment with the stomach, the D.E.S. and the level of the diaphragm, respectively. Water is pumped out of each of these side holes, the pressure required to establish flow at the specific portion of the alimentary tract reflecting the muscular forces that are being measured.

This technique, developed by Drs. Harris and Winans and described in "Quantitation of Lower Esophageal Sphincter Competence", *Gastroenterology*, Vol. 52, No. 5, p. 773 et seq., is subject to some difficulties. For example, if the tube is not centered within the alimentary canal, the observed pressure is reduced because the leakage path through the closed esophagus is reduced on one side or the other of center. The observed data, in this circumstance, is inaccurate.

SUMMARY OF THE INVENTION

These needs are satisfied, to a great extent, through the practice of the invention. Illustratively, a flexible, small diameter tube contains, at predetermined longitudinal spacings, three electrodes each in the form of a short piece of stainless steel tubing, the inner cylindrical surfaces of the electrode being exposed to the hollow tube interior. The tube is partly filled with an electrolyte, preferably an aqueous solution of sodium chloride, and, to prevent galvanic action with the electrolyte, electrical conductors for the electrodes are coupled to the respective outer cylindrical electrode surfaces. All of the electrically conductive elements are covered with a suitable insulating material to prevent short-circuits, stray signals and the like from interfering with the measurements under consideration.

The centrally disposed of the three longitudinally spaced electrodes forms, in effect, a common terminal with each of the two electrodes that are spaced at the opposite longitudinal extremes. Thus, the electrode at the closed, lowermost end of the tube and the central electrode taken with that portion of the column of electrolyte between these two electrodes, form a pressure sensitive variable resistance. Pressure fluctuation in the part of the organ that bears against the portion of the tube which incloses these two electrodes and the associated electrolyte cause the flexible tube to increase and decrease in diameter. These tube diameter changes produce corresponding changes in the resistance between the two electrodes, these electrical resistance changes being related to the applied pressure.

In similar manner, the electrical relationship between the central electrode and the uppermost electrode that is closest to the open end of the tube with the volume of the electrolyte that is between these two electrodes form another pressure sensitive variable resistance that also responds to pressure changes in the adjacent organ.

These two variable resistances each form series connected resistors in two arms of a Wheatstone bridge. The other two series connected resistances that comprise the bridge circuit are external to the patient.

The two series connected variable resistors are a salient feature of the invention. Ordinarily, only one of the four resistances in a Wheatstone bridge circuit is permitted to vary. According to the invention, however, two of the series connected bridge circuit resistances are variable to enable tube compression variation on either side of the central electrode to generate a difference signal. This circuit arrangement is quite novel especially in its application to medical apparatus. Consequently, observed changes in the variable resistances, as registered through electrically unbalanced relationships among the four resistors that comprise the circuit can be related to the bodily pressures under observation.

Naturally, if desired, only one of the variable resistors may be used in the bridge circuit, a fixed resistance being substituted in the arm of the circuit for the uncoupled variable resistor. This circuit arrangement, of course, will depend upon specific pressures to be measured and the characteristics of the organ or cavity under observation.

Thus, there is provided a relatively inexpensive and disposable apparatus that can be used for twenty-four hour gastrointestinal studies with relatively mobile patients, as well as studies of other organs. The apparatus enjoys a small diameter and is reliable and safe to use. For a more complete appreciation of the invention, attention is invited to the following detailed description of a preferred embodiment of the invention taken with the figures of the drawing. The scope of the invention, moreover, is limited only through the claims appended hereto.

DETAILED DESCRIPTION OF THE PREFERRED EMBODIMENT

Figure 1:
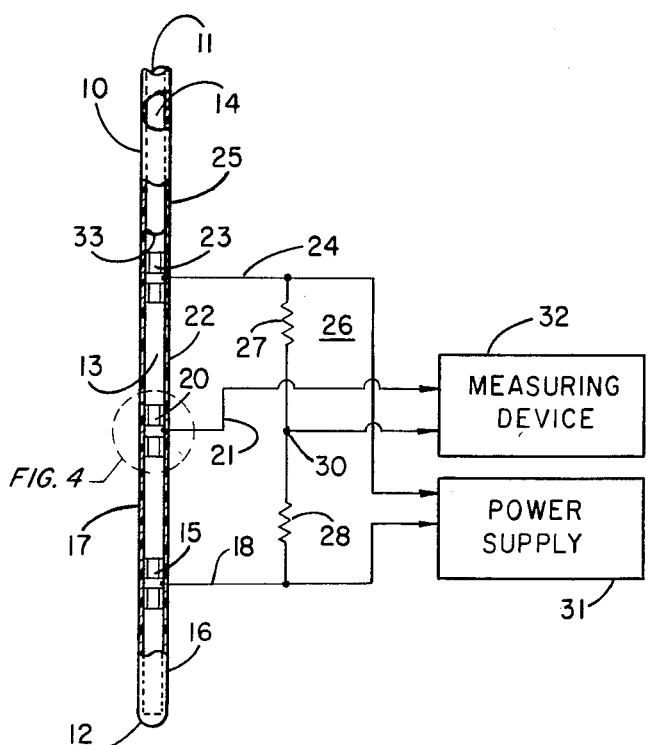
FIG. 1 is a schematic drawing of a typical embodiment of the invention.

An illustrative embodiment of the invention is shown in FIG. 1 of the drawing, in which a flexible elastic walled tube 10, of latex, Silastic, or the like and having an outside diameter of 5 mm (millimeters) and an inside diameter of 2.5 mm, has one open end 11 and, at the opposite end of the tube, a closed end 12. The tube is of an overall length that is sufficient to extend from the stomach (not shown in the drawing) through the esophagus and out of the body of a patient by way of the nasal passages.

Figure 3:
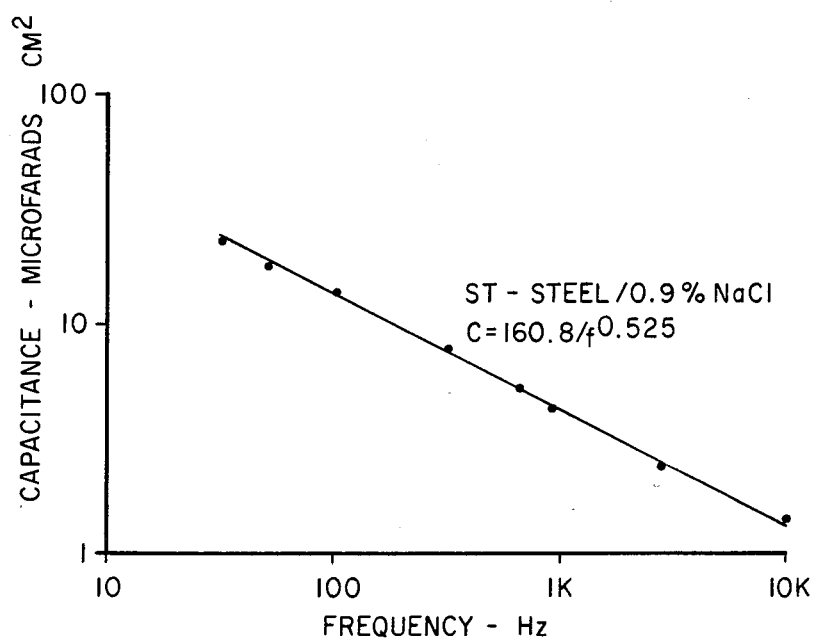
FIG. 3 is a graph of capacitance at the interface between electrolyte and electrode at excitation frequencies above 1 kHz.
Figure 2:
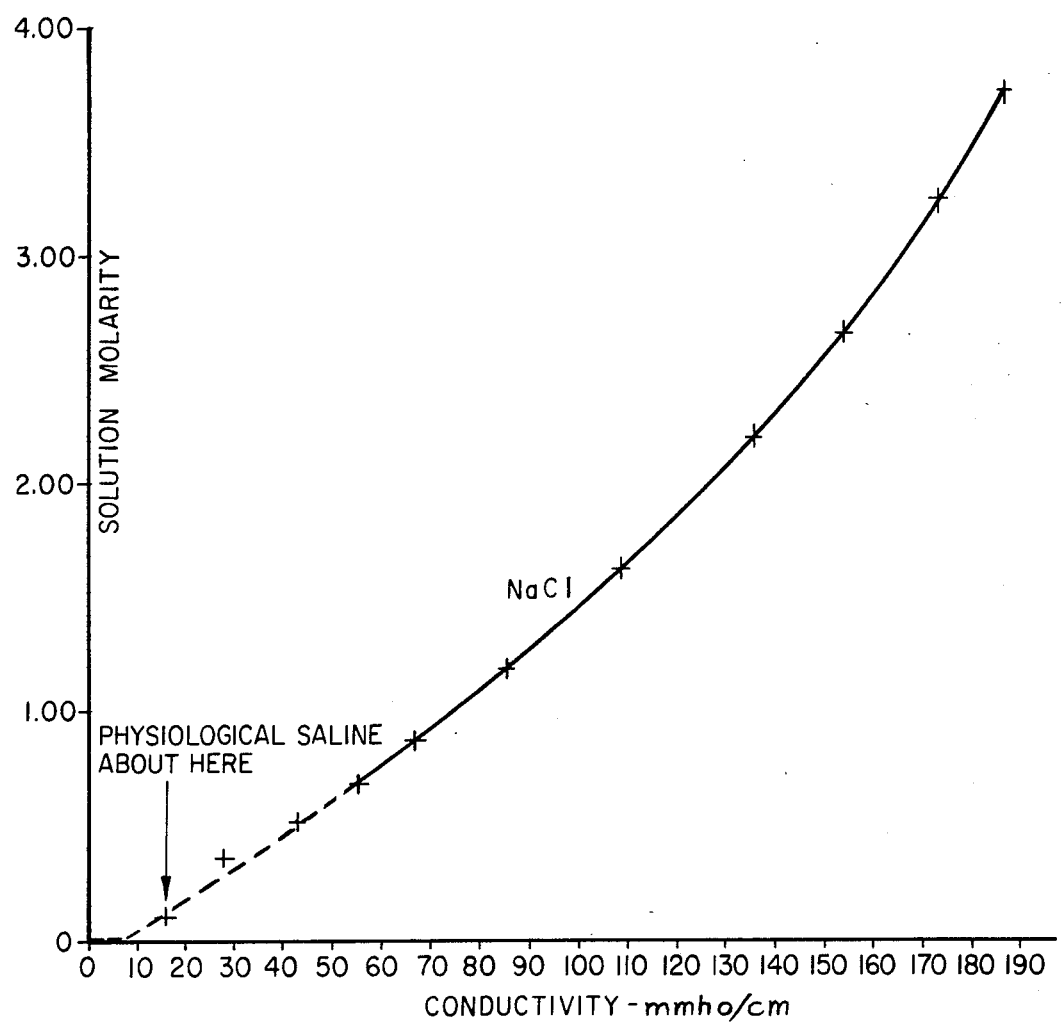
FIG. 2 is a graph of molarity and electrical conductivity for an electrolyte that is suitable for use in connection with the embodiment of the invention shown in FIG. 1.

As shown, the tube 10 is filled with an electrolyte 13. In accordance with a feature of the invention, it has been found that a bubble free sodium chloride solution filling hollow center 14 of the tube 10 enjoys, as shown in FIG. 2, a nearly linear relationship between conductivity and concentration beyond the lower levels, that is, concentrations somewhat above that of a normal saline solution when measured at 2500 Hz excitation frequency. Further in this regard, FIG. 3 shows the very low level of capacitance at the electrolyte/electrode interface at frequencies above 1 kHz.

A cylindrical electrode 15 (FIG. 1) is mounted close to the closed end 12 of the tube 10. The inner surface of the electrode 15 is exposed to the hollow center 14 of the tube 10. Preferably, and to avoid the effect of galvanic action, corrosion, and the like, the electrode is formed from stainless steel. For the purpose of the invention, the electrode 15 can be about one centimeter (cm), or less, in length. The electrode 15 is received in an abutting end 16 of a portion of the tube 10, and the end of the electrode that is oriented toward the open end 11 of the tube being seated in the abutting end of a much softer section of tubing 17.

The outer surface of the electrode 15 is covered with an insulating material in order to prevent electrical conductivity between the electrode and the environment in which the tube 10 is immersed.

An additional feature of the invention is the manner in which an electrically insulated conductor 18 is coupled to the outer surface of the electrode 15. Thus, the dissimilar metals, that is the stainless steel electrode, the copper conductor 18 and the braze, weld or solder that may be used to join the conductor to the electrode ordinarily would be subject to corrosion or galvanic attack if the conductor is secured to the interior surface of the electrode. Accordingly, the conductor 18 is attached to the outer surface of the electrode 15 in order to avoid electrochemical attack from the electrolyte 13.

Another electrode 20 is spaced longitudinally from the electrode 15. The electrode 20, moreover, is mounted in the end of the soft tubing 17 that is opposite to the end of the tubing in which the electrode 15 is received. Save for the relative physical position of the electrode 20, its mounting within the tube 10 and its connection to associated electrical conductor 21 are identical to that which was described with respect to the electrode 15.

A further segment of soft, flexible tubing 22 is joined to the end of the electrode 20 that is not mounted in the soft tubing 17. Further in this regard, the end of the tubing 22 that is opposite to the end that is joined to the electrode 20 secures one end of a third electrode 23. As illustrated, the third electrode 23 and its associated electrical conductor 24 also conform to the description advanced with respect to the electrode 15. The end of the cylindrical electrode 23 that is not lodged in the abutting end of the flexible tubing 22 is received, however, in the end of a less flexible portion 25 of the tube 10.

To complete a Wheatstone bridge circuit 26, a fixed resistor 27 is coupled to the conductor 24 and another fixed resistor 28 is coupled to the conductor 18. Both of the resistors 27,28, however, share a common terminal 30.

For purposes of electrical excitation, a 2500 Hz alternating current power supply 31 is coupled to the conductor 18,24 in order to energize the circuit under consideration. The power supply 31 is coupled to the two "outer" electrodes 15,23.

Two methods of measuring and registering the electrical resistance, or impedance, of the variable resistances formed between the electrodes 15,20 and 20,23 are preferred in the practice of the invention. For example, a constant current impedance measuring device 32 is coupled to the conductor 21 and to the common terminal 30. For this purpose, it has been found that a Lafayette Company impedance converter, fed by a 75 kHz oscillator (not shown in the drawing) will produce accurate voltage fluctuations which correspond to impedance changes that can be demodulated, in turn, to drive a direct current recorder.

Alternatively, a linear differential transformer coupler in a Beckman RM8 dynograph recorder can be used for the measuring device 32. Should this recording apparatus be used, the electrolytic resistances should be a four element system (FIG. 4) with "potential points" similar to the combination used in a high current electric shunt for an ammeter, with a current on the order of 5000 amperes. The shunt is coupled to the circuit and the main current passes through terminals attached to parallel manganin conducting elements, one of which has potential points (or low current connections), that are joined to a low current milliammeter. The low current milliammeter, in turn, is calibrated to produce an output signal that corresponds to the main current.

Briefly, the linear differential transformer in this embodiment of the measuring device 32 has two fixed astatically-wound coils and a small, single turn "pick up" coil that is centrally mounted and capable of micrometer adjustment about a center point. There is, when energized by a 2.5 kHz power supply, a balance point for the "pick up" coil at which the mutual electromagnetic coupling between the energized astatically wound outer coils will not induce a voltage in the "pick up" coil. Small displacements of the central "pick up" coil from this balance point, however, induce a voltage in the "pick up" coil that is proportional to its displacement from the balance point.

Applied to a Wheatstone bridge, this astatic coil combination establishes a phase discrimination that permits the direction and distance of the "pick up" coil from the balance point to be determined. This signal is applied to a "ring demodulator" in order to produce an accurate measurement of the observed electrical inbalance.

Figure 4:
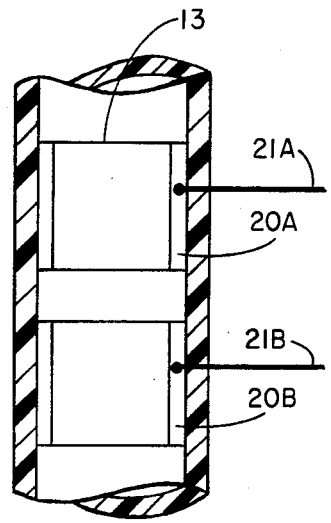
FIG. 4 is a fragmentary view of a different electrode arrangement for practicing the invention.

Used in connection with the apparatus shown in FIG. 1, the 2.5 kHz excitation signal energizes the bridge circuit 26. As mentioned above, it is preferable, when using the differential transformer 32 to divide the centrally disposed electrode 20 into two separate, spaced electrodes 20A and 20B as shown in FIG. 4. It is this inner pair of centrally disposed electrodes 20A and 20B from which the signal that measures the change in electrical resistance is derived through respective conductors 21A and 21B. The advantage provided through this arrangement is an improved baseline stability because there is reduced motion of the electrolyte 13 relative to the electrodes 20A and 20B. In effect, the combination of the electrolyte 13 and the electrodes 20A and 20B introduce capacitances that cause electrical phase shifts between the current and the voltage. Consequently, in terms of electrical elements, the electrolyte device under consideration creates an impedance that is composed of the resistance of the electrolyte 13 and series capacitances.

In operation, the elastic walled tube 10 (FIG. 1) is inserted through the nasal passages, and past the crycopharyngeal sphincter to lodge in the esophagus, with that portion of the tube that spans the electrodes 15,23 next to the distal esophageal sphincter (D.E.S.). The open end 11 of the tube 10 protrudes from the patient and is elevated above the patient. To provide the electrolyte 13, a slightly greater than normal saline solution is poured into the tube 10 to fill to a level of about one inch over the electrode 23, between the electrode and the open end 11. During fill, care must be exercised to make sure that the electrolyte 13 is bubble free.

Upon lodging the tube 10 and filling it with the electrolyte 13, the power supply 31 is activated to energize the bridge circuit 26. The measuring device 32 is adjusted to balance the resistances that comprise the bridge circuit 26 to produce a zero voltage output. These resistances include the series connected resistors 27,28 and the electrolytic resistances provided by the columns of the electrolyte between the electrodes 15,20 and 20,23.

As the distal esophageal sphincter presses in a radially inward direction upon the portion of the tube 10 with which it is in contact, the segments of softer, more pliable tubing 17,22 also collapse inwardly, resulting in decreased tube diameters. These decreases in tube diameter squeeze, or displace, the electrolyte 13 above the preestablished level of meniscus 33. The effect of this decrease in diameter can be likened to the electrical resistance of a wire of length l in which $$\Omega = k \times l/a$$

where $\Omega$ = electrical resistance
$k$ = specific resistance of the wire material
$a$ = cross section areas of the wire
$l$ = length of the wire In this circumstance, the electrical resistance of the electrolyte 13 is inversely proportional to the inner area (or diameter) of the tube 10. Naturally, this change in the electrical resistance, or impedance if capacitive effects are taken into account, is a reflection or measure of the force applied by the D.E.S. to the flexible tubes 17,22. These changes in resistance unbalance the bridge circuit 26 and generate an output signal where no signal, or a different signal, had existed before at the measuring device 32.

This new signal can be calibrated to enable the measuring device 32 to produce an output indication of the D.E.S. pressure in some suitable unit of scientific measurement, of which pressure in millimeters of mercury (mm hg) is typical.

This invention can be adapted to measure pressure in other bodily passageways and cavities that are of scientific and medical interest, for example, the uterus. Thus, there is provided in accordance with the invention a reliable, relatively inexpensive and small diameter apparatus for accurately measuring pressure within the body of a patient who, if not ambulatory, can at least enjoy some degree of relative mobility that was not possible with prior art devices.

I claim:

1. An apparatus for measuring physiological pressures comprising a flexible tube having an open end, a closed end, a hollow interior and an outer surface, an electrode within said tube near said closed tube end, another electrode within said tube spaced from said electrode toward said open tube end, a centrally disposed electrode within said tube generally intermediate of said electrode and said spaced electrode, a pair of series connected electrical resistors, said resistors being coupled to said electrode and said spaced electrode to form a Wheatstone bridge therewith, and a tube portion that is softer and more readily compressed than said flexible tube, said tube portion joining all of said electrodes to said flexible tube and forming a portion of said flexible tube.

2. An apparatus according to claim 1 wherein said central electrode further comprises a pair of electrodes spaced from each other.

3. An apparatus according to claim 2 further comprising a linear differential transformer coupled to said Wheatstone bridge in order to reflect electrical imbalances in said Wheatstone bridge that correspond to physiological pressure measurements.

4. An apparatus according to claim 1 wherein all of said electrodes further comprise stainless steel cylinders, said inner cylindrical surfaces of said cylinders being exposed to said hollow tube interior.

5. An apparatus according to claim 1 further comprising an electrolyte filling said hollow tube interior to a level of about one inch over said spaced electrode toward said open tube end.

6. An apparatus according to claim 1 further comprising a measuring device, said measuring device being electrically coupled to said centrally disposed electrode and to said series connection between said pair of electrical resistors in order to reflect electrical imbalances in said Wheatstone bridge that correspond to physiological pressure measurements.

7. An apparatus according to claim 6 wherein said measuring device further comprises a constant current impedance measuring device.

* * * * *